United States Patent [19]

Martin et al.

[11] Patent Number: 5,496,845
[45] Date of Patent: Mar. 5, 1996

[54] SUSPENSION CONCENTRATE COMPOSITIONS OF ARYLPYRROLE INSECTICIDAL AND ACARICIDAL AGENTS

[75] Inventors: Craig A. Martin, Morrisville, Pa.; Mimi Y. C. Schaaf, Princeton, N.J.

[73] Assignee: American Cyanamid Co., Wayne, N.J.

[21] Appl. No.: 248,996

[22] Filed: May 25, 1994

[51] Int. Cl.$^6$ .................................... A01N 43/36
[52] U.S. Cl. .................... 514/427; 514/422; 514/423; 514/426
[58] Field of Search ................................. 514/422, 423, 514/426, 427

[56] References Cited

U.S. PATENT DOCUMENTS

| | | | |
|---|---|---|---|
| 4,851,421 | 7/1989 | Iwasaki et al. | 514/352 |
| 5,010,098 | 4/1991 | Brown et al. | 514/426 |
| 5,233,051 | 8/1993 | Uhr et al. | 548/526 |

FOREIGN PATENT DOCUMENTS

| | | |
|---|---|---|
| 2076937 | 3/1993 | Canada. |
| 103171-A1 | 3/1984 | European Pat. Off.. |
| 2216798 | 10/1991 | United Kingdom. |

*Primary Examiner*—Allen J. Robinson
*Attorney, Agent, or Firm*—John W. Hogan, Jr.

[57] ABSTRACT

The present invention provides insecticidal and acaricidal suspension concentrate compositions of arylpyrrole compounds.

11 Claims, No Drawings

SUSPENSION CONCENTRATE COMPOSITIONS OF ARYLPYRROLE INSECTICIDAL AND ACARICIDAL AGENTS

BACKGROUND OF THE INVENTION

Certain arylpyrrole compounds, their preparation and use are disclosed in U.S. Pat. Nos. 5,010,098 and 5,233,051; and Canadian Patent Application No. 2,076,937, among others.

While certain suspension concentrates of arylpyrroles are known, for example, see Canadian Patent Application No. 2,076,937, it has been found that upon aging for extended periods of time and/or exposure to elevated temperatures, that those suspension concentrates are not entirely storage stable.

Furthermore, the suspension concentrate composition prepared in Canadian Patent Application No. 2,076,937 has a large ratio of surfactants to arylpyrrole compound. However, the use of high levels of surfactants is not entirely satisfactory because of environmental and economic concerns.

It is therefore an object of the present invention to provide suspension concentrate compositions of arylpyrrole compounds which are physically and chemically stable and therefore have better storageability properties and require the use of less surfactants.

SUMMARY OF THE INVENTION

The present invention provides an insecticidal and acaricidal suspension concentrate composition which comprises about 10% to 50% by weight of a particulate aryl-pyrrole compound having a volume mean diameter of about 0.5 to 4 microns, about 0.1% to 2% by weight of a dispersing agent, about 0.5% to 5% by weight of a steric stabilizer, about 0.1% to 1% by weight of a suspending agent, about 0.01% to 0.5% by weight of a thickening agent, about 5% to 15% by weight of an anti-freeze agent, up to about 1% by weight of an antifoam agent, up to about 0.3% by weight of a preservative and water.

DETAILED DESCRIPTION OF THE PREFERRED EMBODIMENTS

Advantageously, the present invention provides a storage stable insecticidal and acaricidal suspension concentrate composition which comprises 10% to 50% by weight of a particulate arylpyrrole compound having a volume mean diameter of 0.5 to 4 microns, 0.1% to 2% by weight of a dispersing agent, 0.5% to 5% by weight of a steric stabilizer, 0.1% to 1% by weight of a suspending agent, 0.01% to 0.5% by weight of a thickening agent, 5% to 15% by weight of an antifreeze agent, up to 1% by weight of an antifoam agent, up to 0.3% by weight of a preservative and water.

In the suspension concentrate compositions of the present invention, the ratio of the total amount of the dispersing agent and the steric stabilizer to the arylpyrrole compound is preferably about 1:5 to 1:15 and most preferably about 1:8 to 1:10.

Preferred suspension concentrate compositions of this invention are those comprising about 20% to 40% by weight of a particulate arylpyrrole compound having a volume mean diameter of about 1 to 3 microns, 0.5% to 1.5% by weight of a dispersing agent, 1.5% to 3.5% by weight of a steric stabilizer, 0.1% to 1% by weight of a suspending agent, 0.01% to 0.5% by weight of a thickening agent, 5% to 10% by weight of an antifreeze agent, 0.1% to 1% by weight of an antifoam agent, 0.01% to 0.3% by weight of a preservative and water, provided that the ratio of the total amount of the dispersing agent and the steric stabilizer to the arylpyrrole compound is about 1:5 to 1:15.

Uniquely, it has been found that the arylpyrrole suspension concentrate compositions of the present invention are physically and chemically stable for extended periods of time over a wide range of temperatures. Heretofore, arylpyrrole suspension concentrate compositions contained larger particle sizes and/or higher levels of surfactants. The discovery that storage stable suspension concentrate compositions are obtained by reducing the particle size of the arylpyrrole compound and reducing the level of surfactants is especially surprising because generally when smaller particle sizes are used, more surfactants are required to obtain a stable suspension concentrate composition.

Advantageously, the suspension concentrate compositions of the present invention which comprise arylpyrrole particles having a volume mean diameter of about 0.5 to 4 microns are more effective for the control of insects and acarids than the arylpyrrole suspension concentrate compositions of the art.

Arylpyrrole compounds suitable for use in the compositions of this invention have the following structural formula I $$\text{(Structure I: arylpyrrole with substituents X, Y, W, A on pyrrole ring and L, M, R on phenyl ring)}$$

wherein

X is H, F, Cl, Br, I or $C_1$–$C_4$haloalkyl;

Y is F, Cl, Br, I, $C_1$–$C_4$haloalkyl or CN;

W is CN or $NO_2$;

A is $C_1$–$C_4$alkyl optionally substituted with
  one to three halogen atoms,
  one cyano,
  one hydroxy,
  one $C_1$–$C_4$alkoxy,
  one $C_1$–$C_4$alkylthio,
  one phenyl optionally substituted with $C_1$–$C_3$alkyl, $C_1$–$C_3$alkoxy, or one to three halogen atoms,
  one phenoxy optionally substituted with one to three halogen atoms, or
  one benzyloxy optionally substituted with one halogen atom,
$C_1$–$C_4$carbalkoxymethyl,
$C_3$–$C_4$alkenyl optionally substituted with one to three halogen atoms,
cyano,
$C_3$–$C_4$alkynyl optionally substituted with one halogen atom,
di-($C_1$–$C_4$alkyl)aminocarbonyl, or
benzoyl optionally substituted with one to three halogen atoms or one to three $C_1$–$C_4$alkyl groups;

L is H, F, Cl or Br;

M and R are each independently H, $C_1$–$C_3$alkyl, $C_1$–$C_3$alkoxy, $C_1$–$C_3$alkylthio, $C_1$–$C_3$alkylsulfinyl, $C_1$–$C_3$alkylsulfonyl, cyano, F, Cl, Br, I, nitro, $C_1$–$C_3$haloalkyl, $R_1CF_2Z$, $R_2CO$ or $NR_3R_4$, or when M and R are on adjacent positions and taken with the carbon atoms to which they are attached they may form a ring in which MR represents the structure:
—$OCH_2O$—, —$OCF_2O$—, —$OCR_6R_7CR_8R_9O$—, —$OCH_2CH_2$—, —$OCH_2CH_2CH_2$— or —CH=CH—CH=CH—;

Z is $S(O)_n$ or O;

$R_1$ is H, F, $CHF_2$, CHFCl or $CF_3$;

$R_2$ is $C_1$–$C_3$alkyl, $C_1$–$C_3$ alkoxy or $NR_3R_4$;

$R_3$ is H or $C_1$–$C_3$alkyl;

$R_4$ is H, $C_1$–$C_3$alkyl or RSCO;

$R_5$ is H or $C_1$–$C_3$alkyl;

$R_6$, $R_7$, $R_8$ and $R_9$ are each independently hydrogen, halogen or $C_1$–$C_3$alkyl; and n is an integer of 0, 1 or 2.

Preferred arylpyrrole compounds suitable for use in the compositions of the invention are those having the structural formula II

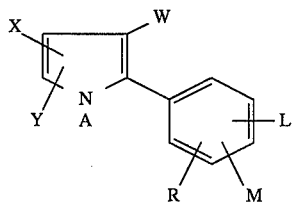

wherein X, Y, W, A, L, M and R are as described above.

More preferred insecticidal and acaricidal arylpyrrole compounds which are particularly useful in the compositions of this invention are those having the structural formula II wherein X and Y are each independently Cl, Br or $CF_3$;

W is CN;

A is $C_1$–$C_4$alkoxymethyl;

L is H or F;

M is H, F, Cl or Br; and

R is F, Cl, Br, $CF_3$ or $OCF_3$.

Especially preferred for use in the suspension concentrate compositions of the present invention is 4- bromo- 2-(p-chlorophenyl)-1-(ethoxymethyl)- 5-(trifluoromethyl)pyrrole-3-carbonitrile.

Dispersing agents suitable for use in this invention include the salts of the condensation products of formaldehyde with the sulfonation products of polycyclic aromatic compounds; the salts of polyacrylic acids; the condensation products of fatty acids or aliphatic amines or amides containing at least about twelve carbon atoms in the molecule with ethylene oxide and/or propylene oxide; fatty acid esters of glycerol, sorbitan, sucrose or pentaerythritol and their condensation products with ethylene oxide and/or propylene oxide; condensation products of fatty alcohols or alkyl phenols with ethylene oxide and/or propylene oxide and their sulfates or sulfonates; and alkali or alkaline earth metal salts of sulfuric or sulfonic acid esters containing at least ten carbon atoms in the molecule, for example sodium lauryl sulfate and dodecylbenzene sulfonate.

Preferred dispersing agents are the salts of the condensation products of formaldehyde with the sulfonation products of polycyclic aromatic compounds such as the salts of the condensation products of formaldehyde with naphthalene sulfonates, petroleum sulfonates and lignin sulfonates with the sodium sulfonate of naphthalene formaldehyde condensates such as MORWET® D425 (Witco, Houston, Tex.), LOMAR® PW (Henkel, Cincinnati, Ohio) and DARVAN® 1 (R.T. Vanderbilt Co., Norwalk, Conn.) being most preferred.

Steric stabilizers are used in the compositions of the present invention to prevent the arylpyrrole particles from sticking together. Steric stabilizers suitable for use include polymers of ethylene oxide and copolymers of ethylene oxide and propylene oxide such as ethylene oxide/propylene oxide block copolymers. Preferred steric stabilizers are butyl-omega-hydroxypoly(oxypropylene) block polymers with poly(oxyethylene) having an average molecular weight in a range of about 2,400 to 3,500 with alpha-butyl-omega-hydroxy-ethylene oxide-propylene oxide block copolymers such as TOXIMUL® 8320 (Stepan Chemical Co., Winder, Ga.), WITCONOL® NS 500 LQ (Witco) and TERGITOL® XD (Union Carbide, Danbury, Conn.) being most preferred.

Suspending agents suitable for use in the compositions of the present invention include natural and synthetic clays and silicates, for example natural silicas such as diatomaceous earths; magnesium silicates such as talcs, magnesium aluminum silicates such as attapulgites and vermiculites; and aluminum silicates such as kaolinites, montmorillonites and micas. Preferred suspending agents are magnesium silicates, magnesium aluminum silicates and aluminum silicates with magnesium aluminum silicates such as VANGEL® ES (R.T.Vanderbilt), VEEGUM® (R.T. Vanderbilt), VEEGUM® T (R.T. Vanderbilt) and GELWHITE® (Southern Clay Products, Gonzales, Tex.) being most preferred.

Thickening agents useful in the suspension concentrate compositions of this invention include natural thickening agents such as xanthan gum, carrageenan, pectin, gum arabic, guar rubber and the like; semisynthetic thickening agents such as the methylation products, carboxyalkylation products and hydroxyalkylation products of cellulose or starch derivatives; and synthetic thickening agents such as polyacrylates, polymaleinates and polyvinylpyrrolidone with xanthan gums such as KELZAN® (Kelco, San Diego, Calif.) and RHODOPOL® 23 (Rhone-Poulenc, Cranbury, N.J.) being preferred thickening agents.

Antifreeze agents suitable for use in the present invention include glycols such as propylene glycol, ethylene glycol and the like with propylene glycol being preferred. Suitable antifoam agents include emulsions of silicone oils, emulsions of fatty alcohols and the like. Preservatives suitable for use in this invention include 1,2-benzisothiazolin-3-one, epichlorohydrin, phenylglycidyl ether, allylglycidyl ether, formaldehyde compositions and the like with 1,2-benzisothiazolin-3-one being preferred.

The suspension concentrate compositions of the present invention may conveniently be prepared by admixing the desired arylpyrrole compound, dispersing agent, steric stabilizer, suspending agent, antifreeze agent and water until a homogeneous mixture is obtained, then milling the homogeneous mixture to obtain a mill base wherein the arylpyrrole compound particles have a volume mean diameter of about 0.5 to 4 microns. A mixture of the thickening agent in water and water are then added to the mill base and mixing is continued to obtain the desired suspension concentrate composition of the present invention.

The suspension concentrate compositions of this invention preferably have a pH of about pH 5 to pH 9 and more preferably about pH 6 to pH 8. Acids suitable for use in buffering the compositions of the present invention include hydrochloric acid, phosphoric acid, sulfuric acid, acetic acid, propionic acid and the like with acetic acid being preferred.

In order to facilitate a further understanding of the invention, the following examples are presented to illustrate more specific details thereof. The invention is not to be limited thereby except as defined in the claims.

EXAMPLE 1

Preparation of suspension concentrate compositions

Propylene glycol (331 g), a 17% 1,2-benzisothiazolin-3-one solution (PROXEL® GXL, ICI Americas) (6.35 g), a 30% silicone emulsion (AF 30 IND, Harcros Chemical Co.) (29.9 g), alpha-butyl-omega-hydroxylethylene oxide/propylene oxide block copolymer (TOXIMUL® 8320, Stepan Chemical Co.) (132.5 g), sodium sulfonate of naphthalene formaldehyde condensate (MORWET® D425, Witco) (44 g), magnesium aluminum silicate (VANGEL® ES, R.T. Vanderbilt) (22.2 g) and 4-bromo-2-(p-chlorophenyl)-1-(ethoxymethyl)-5-(trifluoromethyl)pyrrole- 3-carbonitrile (1,542 g, 90% real) are added sequentially with stirring to water (976 g). The resultant mixture is stirred until homogeneous and passed through a wet milling device to obtain a mill base wherein the arylpyrrole particles have a volume mean diameter of about 1.5 microns. The mill base is charged into a vessel, agitated and adjusted to a pH of pH 6.5 to pH 7.2 with acetic acid. A 1% xanthan gum gel (662 g) prepared from xanthan gum (6.8 g), a 17% 1,2-benzisothiazolin-3-one solution (PROXEL® GXL, ICI Americas) (0.45 g) and water (654.75 g) and water (659 g) are added to the pH adjusted mill base and mixing is continued to obtain the desired suspension concentrate composition identified as composition 1 in Table II.

Using essentially the same procedure, but using the ingredients listed in Table I, the suspension concentrate compositions identified as compositions 2–21 in Table II may be prepared.

f. alpha-butyl-omega-hydroxy-ethylene oxide-propylene oxide block copolymer (TOXIMUL® 8320)

g. ethylene oxide/propylene oxide block copolymer (PLURONIC® P104, BASF Corp., Wyandotte, Mich.)

Suspending Agent h. magnesium aluminum silicate (VANGEL® ES)

i. synthetic clay (LAPONITE® RD, Laporte, Rolling Meadows, Ill.)

Thickening Agent j. xanthan gum (KELZAN®)

k. xanthan gum (RHODOPOL® 23)

Antifreeze Agent l. propylene glycol m. ethylene glycol

Antifoam Agent n. 30% silicone emulsion (AF 30 IND)

Preservative o. 17% 1,2-benzisothiazolin-3-one solution (PROXEL® GXL)

Acid p. acetic acid

TABLE II

Suspension Concentrate Compositions

Ingredient/wt/wt %

| Composition Number | Arylpyrrole Compound | Dispersing Agent | Steric Stabilizer | Suspending Agent | Thickening Agent | Antifreeze Agent | Antifoam Agent | Preservative | Acid | Water |
|---|---|---|---|---|---|---|---|---|---|---|
| 1 | a/35 | d/1.0 | f/3.0 | h/0.5 | j/0.15 | l/7.5 | n/0.68 | o/0.15 | p/0.2 | 51.82 |
| 2 | a/24.3 | d/0.7 | f/2.09 | h/0.35 | j/0.20 | l/7.5 | n/0.47 | o/0.10 | p/0.14 | 64.15 |
| 3 | a/24.3 | e/0.7 | f/2.09 | h/0.35 | j/0.20 | l/7.5 | n/0.47 | o/0.10 | p/0.14 | 64.15 |
| 4 | a/24.3 | d/0.7 | g/2.09 | h/0.35 | j/0.20 | l/7.5 | n/0.47 | o/0.10 | p/0.14 | 64.15 |
| 5 | a/24.3 | e/2.0 | g/1.5 | h/0.35 | j/0.20 | m/7.5 | n/0.47 | o/0.10 | p/0.14 | 63.44 |
| 6 | a/24.3 | e/2.0 | g/1.5 | i/0.35 | j/0.20 | m/7.5 | n/0.47 | o/0.10 | p/0.14 | 63.44 |
| 7 | a/24.3 | e/2.0 | g/1.5 | h/0.35 | k/0.20 | m/7.5 | n/0.47 | o/0.10 | p/0.14 | 63.44 |
| 8 | a/24.3 | d/1.5 | f/3.3 | i/0.5 | k/0.23 | l/7.5 | n/0.75 | o/0.10 | p/0.15 | 61.67 |
| 9 | a/35 | e/1.0 | f/3.0 | h/0.5 | j/0.15 | l/7.5 | n/0.68 | o/0.15 | p/0.2 | 51.82 |
| 10 | a/35 | d/1.0 | g/3.0 | h/0.5 | j/0.15 | l/7.5 | n/0.68 | o/0.15 | p/0.2 | 51.82 |
| 11 | a/35 | e/0.9 | g/1.5 | h/0.5 | j/0.15 | m/7.5 | n/0.5 | o/0.15 | p/0.2 | 53.60 |
| 12 | a/35 | e/2.0 | f/5.0 | h/0.3 | k/0.1 | m/5.0 | n/1.0 | o/0.15 | p/0.2 | 51.25 |
| 13 | a/45 | e/2.0 | f/5.0 | h/0.3 | k/0.1 | m/5.0 | n/1.0 | o/0.15 | p/0.2 | 41.25 |
| 14 | a/45 | d/1.5 | g/3.0 | h/0.3 | k/0.1 | m/5.0 | n/1.0 | o/0.15 | p/0.2 | 43.75 |
| 15 | a/12 | d/0.5 | f/1.7 | h/1.0 | j/0.3 | l/10.0 | n/0.3 | o/0.3 | p/0.05 | 73.85 |
| 16 | a/12 | d/0.5 | f/1.7 | h/0.7 | j/0.5 | l/10.0 | n/0.3 | o/0.3 | p/0.05 | 73.95 |
| 17 | a/17.5 | d/0.5 | f/2.0 | h/0.7 | j/0.3 | l/10.0 | n/0.3 | o/0.3 | p/0.05 | 68.35 |
| 18 | b/17.5 | d/0.5 | f/2.0 | h/0.7 | j/0.3 | l/10.0 | n/0.3 | o/0.3 | p/0.05 | 68.35 |
| 19 | b/12 | d/0.5 | f/1.7 | h/1.0 | j/0.3 | l/10.0 | n/0.3 | o/0.3 | p/0.05 | 73.85 |
| 20 | c/17.5 | d/0.5 | f/2.0 | h/0.7 | j/0.3 | l/10.0 | n/0.3 | o/0.3 | p/0.05 | 68.35 |
| 21 | c/17.5 | d/0.5 | f/2.0 | h/0.7 | j/0.3 | l/10.0 | n/0.3 | o/0.3 | p/0.05 | 68.35 |

TABLE I

Arylpyrrole Compound a. 4-bromo-2-(p-chlorophenyl)-1-(ethoxymethyl)- 5-(trifluoromethyl)pyrrole-3-carbonitrile b. 1-benzoyl-4-bromo-2-(p-chlorophenyl)- 5-(trifluoromethyl)pyrrole-3-carbonitrile c. 4-chloro-2-(p-chlorophenyl)-1-(ethoxymethyl)- 5-(trifluoromethyl)pyrrole-3-carbonitrile Dispersing Agent d. sodium sulfonate of naphthalene formaldehyde condensate (MORWET® D425)

e. sodium salt of lignin sulfonate

Steric Stabilizer

EXAMPLE 2

Stability of suspension concentrate compositions

The stabilities of suspension concentrate composition numbers 1 and 2 from Table II are evaluated by storing samples of the compositions for three, six and six months at 45° C., 37° C. and 25° C., respectively, then measuring (1) the percent of arylpyrrole recovered from the samples by high performance liquid chromatography analyses, (2) the volume mean diameter of the arylpyrrole particles present in the samples with a Malvern particle sizer, and (3) the viscosity of the samples with a Brookfield viscometer (#2 spindle, room temperature, 60 rpm). The method used to measure the percent arylpyrrole recovered from the samples has an experimental error of ± 2%. The results are summarized in Table III.

As can be seen from the data in Table III, the suspension concentrate compositions of the present invention are physically and chemically stable for extended periods of time at various temperatures.

TABLE III

Stability of Suspension Concentrate Compositions

| | Storage Conditions | | | |
|---|---|---|---|---|
| | Initial | 45° C./ 3 months | 37° C./ 6 months | 25° C./ 6 months |
| Composition 1 | | | | |
| Percent Arylpyrrole Recovered | 100.0 | 100.6 | 100.1 | 99.6 |
| Volume Mean Diameter of Arylpyrrole Particles (microns) | 1.26 | 1.92 | 1.68 | 1.37 |
| Viscosity (cps) | 223 | 193 | 220 | 229 |
| Composition 2 | | | | |
| Percent Arylpyrrole Recovered | 100.0 | 101.5 | 101.4 | 101.0 |
| Volume Mean Diameter of Arylpyrrole Particles (microns) | 1.31 | 2.05 | 1.80 | 1.42 |
| Viscosity (cps) | 205 | 202 | 209 | 215 |

What is claimed is:

1. A stable suspension concentrate composition which comprises about 10% to 50% by weight of a particulate aryl-pyrrole compound having a volume mean diameter of about 0.5 to 4 microns and having the structural formula

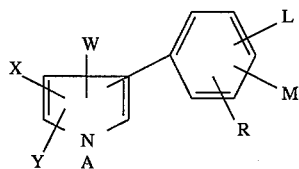

wherein

X is H, F, Cl, Br, I or $C_1$–$C_4$haloalkyl;

Y is F, Cl, Br, I $C_1$–$C_4$haloalkyl or CN;

W is CN or $NO_2$;

A is $C_1$–$C_4$alkyl optionally substituted with
one to three halogen atoms,
one cyano,
one hydroxy,
one $C_1$–$C_4$alkoxy,
one $C_1$–$C_4$alkythio,
one phenyl optionally substituted with $C_1$–$C_3$alkyl, $C_1$–$C_3$alkoxy, or one to three halogen atoms,
one phenoxy optionally substituted with one to three halogen atom, or
one benzyloxy optionally substituted with one halogen atom,
$C_1$–$C_4$carbalkoxymethyl,
$C_3$–$C_4$alkenyl optionally substituted with one to three halogen atoms,
cyano,
$C_3$–$C_4$alkynyl optionally substituted with one halogen atom, di-($C_1$–$C_4$alkyl)aminocarbonyl, or
benzoyl optionally substituted with one to three halogen atoms or one to three $C_1$–$C_4$alkyl groups:

L is H, F, Cl or Br;

M and R are each independently H, $C_1$–$C_3$alkyl, $C_1$–$C_3$alkoxy, $C_1$–$C_3$alkylthio, $C_1$–$C_3$-alkylsulfinyl, $C_1$–$C_3$alkylsulfonyl, cyano, F, Cl, Br, I, nitro, $C_1$–$C_3$haloalkyl, $R_1CF_2Z$, $R_2CO$ or $NR_3R_4$, or when M and R are on adjacent positions and taken with the carbon atoms to which they are attached they may form a ring in which MR represents the structure:

—$OCH_2O$—, —$OCF_2O$—, —$OCR_6R_7CR_8R_9O$—,
—$OCH_2CH_2$—, —$OCH_2CH_2CH_2$— or
—CH=CH—CH=CH—;

Z is $S(O)_n$ or O;

$R_1$ is H, F, $CHF_2$, $CHFCl$, or $CF_3$;

$R_2$ is $C_1$–$C_3$alkyl, $C_1$–$C_3$ alkoxy, or $NR_3R_4$;

$R_3$ is H or $C_1$–$C_3$alkyl;

$R_4$ is H or $C_1$–$C_3$alkyl or $R_5CO$;

$R_5$ is H or $C_1$–$C_3$alkyl;

$R_6R_7R_8$ and $R_9$ are each independently hydrogen, halogen or $C_1$–$C_3$alkyl; and n is an integer of 0, 1 or 2, about 0.1% to 2% by weight of a dispersing agent selected from the group consisting of the salts of the condensation products of formaldehyde with the sulfonation products of polycyclic aromatic compounds; the salts of polyacrylic acids; the condensation products of fatty acids or aliphatic amines or amides containing at least about twelve carbon atoms in the molecule with ethylene oxide and/or propylene oxide; fatty acid esters of glycerol, sorbitan, sucrose or pentaerythritol and their condensation products with ethylene oxide and/or propylene oxide; condensation products of fatty alcohols or alkyl phenols with ethylene oxide and/or propylene oxide and their sulfates or sulfonates; and alkali or alkaline earth metal salts of sulfuric or sulfonic acid esters containing at least ten carbon atoms in the molecule, about 0.5% to 5% by weight of a steric stabilizer selected from the group consisting of polymers of ethylene oxide and copolymers of ethylene oxide and propylene oxide, about 0.1% to 1% by weight of a suspending agent consisting essentially of one or more natural or synthetic clays or silicates, about 0.01% to 0.5% by weight of a thickening agent selected from the group consisting of xanthan gum, carrageenan, pectin, gum arabic, guar rubber, the methylation products, carboxyalkylation products and hydroxyalkylation products of cellulose or starch derivatives, polyacrylates, polymaleinates and polyvinylpyrrolidone with xanthan gums, about 5% to 15% by weight of an anti-freeze agent comprising a glycol, up to about 1% by weight of an antifoam agent comprising an emulsion of a silicone oil or an emulsion of a fatty alcohol, up to about 0.3% by weight of a preservative selected from the group consisting of 1,2-benzisothiazolin-3-one, epichlorohydrin, phenylglycidyl ether, allylglycidyl ether, and formaldehyde compositions, and water.

2. The composition according to claim 1 wherein the ratio of the total amount of the dispersing agent and the steric stabilizer to the arylpyrrole compound is about 1:5 to 1:15.

3. The composition according to claim 2 wherein the ratio is about 1:8 to 1:10.

4. The composition according to claim 2 which comprises 20% to 40% by weight of a particulate arylpyrrole compound having a volume mean diameter of 1 to 3 microns, 0.5% to 1.5% by weight of a dispersing agent, 1.5% to 3.5% by weight of a steric stabilizer, 0.1% to 1% by weight of a suspending agent, 0.01% to 0.5% by weight of a thickening agent, 5% to 10% by weight of an antifreeze agent, 0.1% to 1% by weight of an antifoam agent, 0.01% to 0.3% by weight of a preservative and water.

5. The composition according to claim 1 wherein the dispersing agent is a salt of the condensation products of formaldehyde with the sulfonation products of polycyclic aromatic compounds; the steric stabilizer is an ethylene oxide/propylene oxide block copolymer; the suspending agent is selected from the group consisting of a magnesium aluminum silicate, a magnesium silicate and an aluminum silicate; the thickening agent is selected from the group consisting of xanthan gum, carrageenan, pectin, gum arabic and guar rubber; and the antifreeze agent is a glycol.

6. The composition according to claim 5 wherein the dispersing agent is the sodium sulfonate of naphthalene formaldehyde condensates, the steric stabilizer is an alpha-butyl-omega-hydroxy-ethylene oxide-propylene oxide block copolymer, the suspending agent is a magnesium aluminum silicate, the thickening agent is xanthan gum, and the antifreeze agent is propylene glycol.

7. The composition according to claim 1 having a pH of pH 5 to pH 9.

8. The composition according to claim 7 wherein the pH is pH 6 to pH 8.

9. The composition according to claim 1 wherein the compound has the structural formula

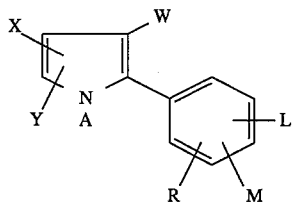

10. The composition according to claim 9 wherein

X and Y are each independently Cl, Br or $CF_3$;

W is CN;

A is $C_1$–$C_4$ alkoxymethyl;

L is H or F;

M is H, F, Cl or Br; and

R is F, Cl, Br, $CF_3$ or $OCF_3$.

11. The composition according to claim 10 wherein the compound is 4-bromo-2-(p-chlorophenyl)-1-(ethoxymethyl)- 5-(trifluoromethyl)pyrrole-3-carbonitrile.

* * * * *